(12) United States Patent
Eberle

(10) Patent No.: US 8,335,664 B2
(45) Date of Patent: Dec. 18, 2012

(54) METHOD AND SYSTEM FOR ARTIFACT REDUCTION

(75) Inventor: Wolfgang Eberle, Leuven (BE)

(73) Assignee: IMEC (BE)

( * ) Notice: Subject to any disclaimer, the term of this patent is extended or adjusted under 35 U.S.C. 154(b) by 725 days.

(21) Appl. No.: 12/562,876

(22) Filed: Sep. 18, 2009

(65) Prior Publication Data

US 2010/0068751 A1 Mar. 18, 2010

Related U.S. Application Data

(60) Provisional application No. 61/098,166, filed on Sep. 18, 2008.

(51) Int. Cl.
*G06F 15/00* (2006.01)
*C12M 1/34* (2006.01)

(52) U.S. Cl. ...................................... 702/190; 435/287.1

(58) Field of Classification Search .................. 702/190; 435/287.1

See application file for complete search history.

(56) References Cited

U.S. PATENT DOCUMENTS 6,114,164 A * 9/2000 Dennis et al. .............. 435/286.1
6,526,365 B1 * 2/2003 Marino et al. ................ 702/111

OTHER PUBLICATIONS

O'Keeffe, Derek T. et al., "Stimulus Artifact Removal Using a Software-Based Two-Stage Peak Detection Algorithm", Journal of Neuroscience Methods, vol. 109 (2001), pp. 137-145.

* cited by examiner

*Primary Examiner* — Bryan Bui
(74) *Attorney, Agent, or Firm* — McDonnell Boehnen Hulbert & Berghoff LLP

(57) ABSTRACT

A method is presented for obtaining characteristics of a target physical entity by providing an excitation signal to the target physical entity and simultaneously measuring the response of the target physical entity. Analog signal processing is performed on the measured response to eliminate artifacts arising from a signal path outside the target physical entity and determining the characteristics from the signal processed measured response. The excitation signal and the analog signal processing are selected such that after analog signal processing of the measured signal, the analog measured signal contains artifacts which are localized in time.

16 Claims, 9 Drawing Sheets

Providing an excitation signal to a target physical system and simultaneously measuring the response of the target physical system

↓

Performing signal processing on the measured response to eliminate artifacts that arise from the signal path outside the physical system

↓

Determining the characteristics from the signal processed measured response

METHOD AND SYSTEM FOR ARTIFACT REDUCTION

CROSS-REFERENCE TO RELATED APPLICATIONS

This application claims priority to U.S. Provisional Application Ser. No. 61/098,166 filed Sep. 18, 2008, the contents of which are incorporated by reference herein in its entirety.

BACKGROUND

Since EMG, ENG and EEG signals are all fundamentally electrophysiological signals, a technique developed to remove stimulus artifact contamination present in any of the biopotential recording, may be modified and used to remove artifact from the other types. These techniques may reduce the effect of stimulus artifact and improve the fidelity of the recorded signals. These stimulus artifacts are due to direct coupling path between the closely spaced electrodes. However, most techniques suffer from an inability to adapt to the dynamic nature of stimulation artifact, due to the non-linearities of the stimulation procedure and hence suffer residual artifact.

Both analog and digital (software-based) techniques have been developed to reduce these artifacts.

An overview of such possible hardware and software techniques have been made in Derek T. O'Keeffe et al. in document "Stimulus artifact removal using a software-based two-stage peak detection algorithm" published in Journal of Neuroscience Methods 109 (2001) 137-145 but all these techniques suggest or reveal a lack of one or two properties to make them widely applicable.

In particular, deep brain stimulation (DBS) is a last resort therapy for drug treatment-resistant neurological diseases such as Parkinson's, obsessive-compulsive disorders, and many more. The classical mm-size electrode solution (e.g. of Medtronic®) supports only weak spatial resolution and is operated in an open-loop stimulation approach only. Such large electrodes usually measure biopotentials averaged on a huge number of electrogenic cells. Such signals present low frequency waves representative of large scale cells activity.

$\mu$m-size electrode contacts and both stimulation and recording capabilities provide a better understanding of the actual working principles of DBS, development of new therapies, and in situ monitoring the operation of chronically implanted DBS electrodes.

The use of such $\mu$m-size electrode contacts permits the measurement of the action potentials originating from a single electrogenic cell, or from a limited number of cells, so that the action potentials of individual cells can be distinguished.

In such small neural probes, simultaneous stimulation and recording lead to large artifact signals due to direct coupling path between the closely spaced electrodes. Moving to $\mu$m-size electrodes worsens the situation. Stimulation signals in the —range of 0.1-to-1 V are superimposed on the neural activity recordings in the 10-to-100 $\mu$V range. High-gain analog electronics is required to amplify the weak signals but gets saturated by the high stimulation artifacts. Saturation and recovery from it can result in the loss of recording information over a multiple of the stimulus duration time.

BRIEF SUMMARY

The present disclosure is related to a method and a system (apparatus) able to compensate or reduce stimulation artifact from recorded signals.

In particular, the present disclosure is related to a method and a system (apparatus) able to remove or reduce stimulation artifacts present in action potential signals evoked by electrical stimulation.

More particularly the preferred method of the disclosure is used in the measurement of action potential originating from a single, a few electrogenic cells (i.e. the action potentials originating from the different cells can still be individually distinguished).

The present disclosure provides a method for obtaining characteristics of a target physical entity. The method includes providing an excitation signal to the target physical entity and simultaneously measuring the response of the target physical entity; performing analog signal processing on the measured response to eliminate artifacts that arise from a signal path outside the target physical entity (system) and determining the characteristics from the signal processed measured response whereby the excitation signal and the analog signal processing are selected such that after analog signal processing of the measured signal, the analog measured signal contains artifacts which are localized in time.

The analog signal processing step further includes the subtraction of a predetermined signal representative or corresponding to the signal path outside the physical entity to the measured signal. Whereby preferably the predetermined signal is being estimated by an initial training phase. For example, the predetermined signal is estimated by low-pass filtering a measured response in a training phase.

The method further includes estimating a residual artifact in the processed analog signal. In an embodiment, an additional training phase is performed each time the residual artifact is above a predetermined threshold, defining a new predetermined signal to be used in subsequent stimulation sequences.

In an embodiment, the analog signal processing is supplemented by a digital signal compensation. Preferably, the digital compensation is obtained by interpolation, in particular three points interpolation, and/or blanking techniques and/or adapting filtering methods.

In an embodiment, the excitation of the target physical entity and the measurement of the response are done via electrodes.

In an embodiment, the excitation signal can be a voltage pulse, a current pulse or an RF pulse.

In an embodiment, the characteristics to be obtained are the electrical response of individual electrogenic cells to electrical stimuli corresponding to the excitation signal.

In an embodiment, the target physical entity is a single or a group of electrogenic cells. For example, the target physical entity (system) is in vivo or in vitro single or limited group of neurons. For example, the target physical system is bacteria, algae, fungi, protists or plants.

In an embodiment, a system or architecture is presented for implementing the method. The system includes an excitation source for providing an excitation signal to the target physical entity and a sensor for simultaneously measuring the response of the target physical entity; signal processing element for performing signal processing on the measured response to eliminate artifacts that arise from a signal path outside the target physical entity and a computing element for determining the characteristics from the signal processed measured response. The system allows the selection of a predetermined excitation pulse and the signal processing element is selected such that after analog signal processing of the measured signal, the analog measured signal contains artifacts which are localized in time. Preferably, the excitation source and sensor of the system are located on a $\mu$m-sized probe able to discriminate individual action potential originating from a limited number of electrogenic cells.

FIGURE KEYS ARE

Figure 1:
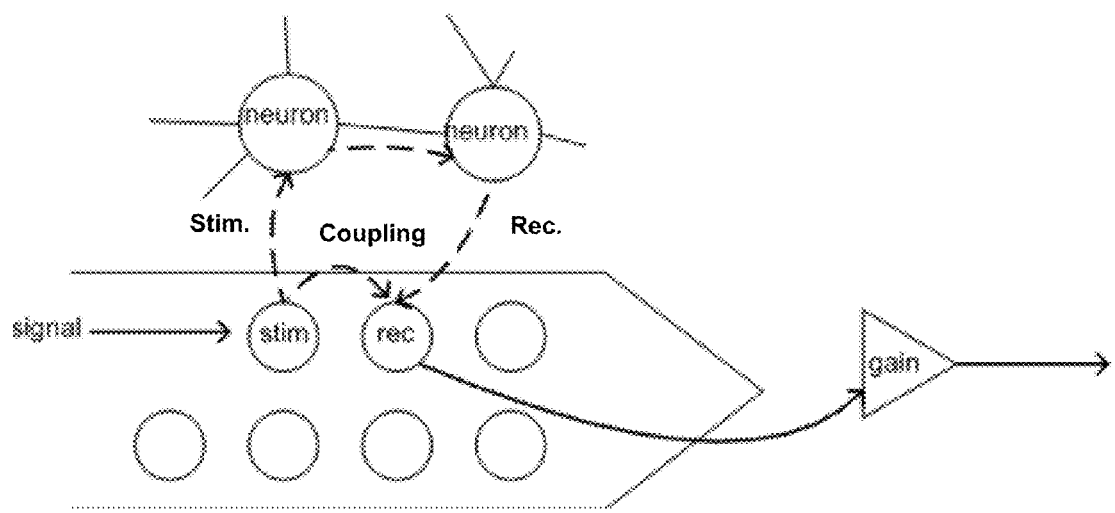
FIG. 1 is a representation of the pathways of stimulation and recording with the direct coupling between electrodes of a neural probe leading to stimulation artifacts.

1. Final corrected signal
2. Digital compensator
3. Analog corrected signal
4. Raw input signal
5. Target physical entity
6. Measuring electrode
7. Stimulating electrode
8. μ-size probe comprising a stimulating and a measuring electrode
9. Analog stimulus generator
10. Digital stimulus generator
11. Digital process control unit
12. Digital template signal
13. Analog template signal generator
14. Analog template signal
15. Analog read-out unit comprising analog compensator
16. Digital estimator
17. Residual artifact digital estimator
18. Digital compensation signal estimate
19. Stimulus signal
20. Analog to digital converter (ADC)
21. Analog corrected digital signal.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

For the purpose of this disclosure, the term "excitation" used in the present document has the same meaning compared to the term "stimulation" and both can thus be used interchangeably. The terms "measuring", "measured signal" have the same meaning compared to "recording" or "recorded signal" and can thus also be used interchangeably.

Different preferred aspects of the present embodiment are described in FIGS. 7 to 10

According to the present embodiment, a method for obtaining characteristics of a target physical entity (system) is disclosed, the method including the steps of providing an excitation signal to the target physical entity (system) and simultaneously measuring the response of the target physical entity (system), performing signal processing on the measured response to eliminate artifacts that arise from a signal path outside the target physical entity (system), determining the characteristics from the signal processed measured response, characterized in that the excitation signal is selected and the analog signal processing is selected such that after analog signal processing of the measured signal, the analog measured signal contains artifacts which are localized in time.

By localized in time, it is meant that the time duration of an eventual residual artifact in the analog processed signal has been reduced in comparison with the duration of the artifact in the measured signal.

Preferably, the excitation of the target physical entity (system) and the measurement of the response is done via a physical interface. The physical interface can be an electrode or an array of electrodes, a transducer or an array of transducers.

The excitation signal can be a voltage pulse, a current pulse or an RF pulse.

The signal path outside the target physical entity (system) is the signal originating from the direct coupling between a stimulus electrode and a measuring electrode. By direct coupling, it is meant the passive electrical conduction of the media around the physical entity, excluding the signal originating from electrical activity of the physical entity.

The present embodiment is particularly useful in the measurement of the characteristics such as shape and intensity of the electrical response of individual electrogenic cells to electrical stimuli.

Preferably, electrical electrodes are used for applying the stimulus and measuring the response, and said electrodes are located on μm-sized probe, so that the spatial resolution of the measured response is able to discriminate the electrical response of individual electrogenic cells to electrical stimuli.

Preferably, said signal processing step further comprises digital signal processing (step) for filtering out the artifacts.

Preferably, said signal processing step includes analog signal processing followed by digital signal processing. The processed analog signal is converted to a digital signal by an analog to digital converter.

Preferably, a substantial part of the analog processed signal is within the dynamic range of the analog digital convertor.

Preferably, said analog signal processing step comprises a subtraction step of a predetermined signal representative or corresponding to the signal path outside the physical system. This further step is an analog template subtraction.

The method can further comprise the step of amplifying the processed analog signal after the subtraction step and before analog to digital conversion.

Preferably, the excitation signal is a broadband pulse. In a further particular embodiment, the excitation signal is a triangular pulse.

The target physical entity (system) can be vertebrate or invertebrate in vivo or in vitro neural tissue(s), muscle fibers, pancreatic cells, or the like.

Preferably, the target physical entity is a single or a group of electrogenic cells, such as vertebrate or invertebrate in vivo or in vitro neurons.

Furthermore, the target physical system can be bacteria, algae, fungi, protists or plants.

More preferably, the target physical entity (system) is in vivo or in vitro neural tissue.

Even more preferably, the target physical entity (system) is in vivo or in vitro single or limited group of neurons. By limited group, it is meant that individual action potential from the different neurons can still be differentiated from the average neural signal.

In another embodiment, a system or architecture for obtaining or retrieving characteristics of a target physical system is disclosed, the system including an excitation source for providing an excitation signal to the target physical entity (system) and a sensor for simultaneously measuring the response of the target physical entity (system), signal processing element for performing signal processing on the measured response to eliminate artifacts that arise from a signal path outside the target physical entity (system), a computing element for determining the characteristics from the signal processed measured response, wherein the system allows the selection of a predetermined excitation pulse and the signal processing element is selected such that after analog signal processing of the measured signal, the analog measured signal contains artifacts which are localized in time. By localized in time, it is meant that the artifacts have been reduced except at localized time place or regions.

Preferably, said signal processing element comprises an analog signal processing element and a digital signal processing element.

Preferably, said signal processing element is further selected such that it further comprises a digital signal processing for filtering out (or arranged to filter out) the artifacts.

Preferably, said system further comprises an analog to digital converter. Preferably, the analog signal processing element is selected such that a substantial part of the analog processed signal is within the dynamic range of the analog digital convertor.

Preferably, said analog signal processing element is selected such that it comprises subtraction of a predetermined signal representative for the signal path outside the physical system. This is further called analog template subtraction.

Preferably, said system comprises an amplifier between the analog signal processing element and the analog digital converter.

Preferably, the excitation source is selected to deliver is a broadband pulse. In a particular embodiment, the excitation signal is a triangular pulse.

In small neural probes, as represented in FIG. 1, simultaneous stimulation and recording lead to large artifact signals due to direct coupling path between the closely-spaced electrodes. Moving to µm-size electrodes worsens the situation.

Figure 2:
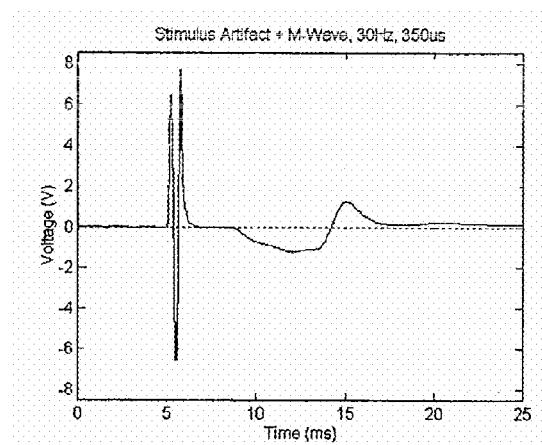
FIG. 2 is representing the general behaviour of a recorded ENG signal (m-wave) after the contamination of a stimulus artifact.

An example of a recorded signal not treated by the method of the present embodiment is shown as an example in FIG. 2.

As an example, high-resolution neural probes with electrode contacts between 4 µm and 50 µm using micro-fabrication techniques have been fabricated. Probes for rat cortex experiments have a 200×200 µm$^2$ cross-section, a 2-mm shaft with an aim of 9-mm for rat DBS, 10 contacts, and a thermal sensor. Fabrication is based on a micro-fabrication process on 6-inch silicon wafers. The probes have Au electrodes and biocompatible Parylene C-coatings.

Stimulation signals in the range of 0.1-to-1 V are preferably superimposed on the neural activity recordings in the 10-to-100 µV range. High-gain analog electronics is required to amplify the weak signals but gets saturated by the high stimulation artifacts. Saturation and recovery from it can result in the loss of recording information over a multiple of the stimulus duration time.

Figure 7:
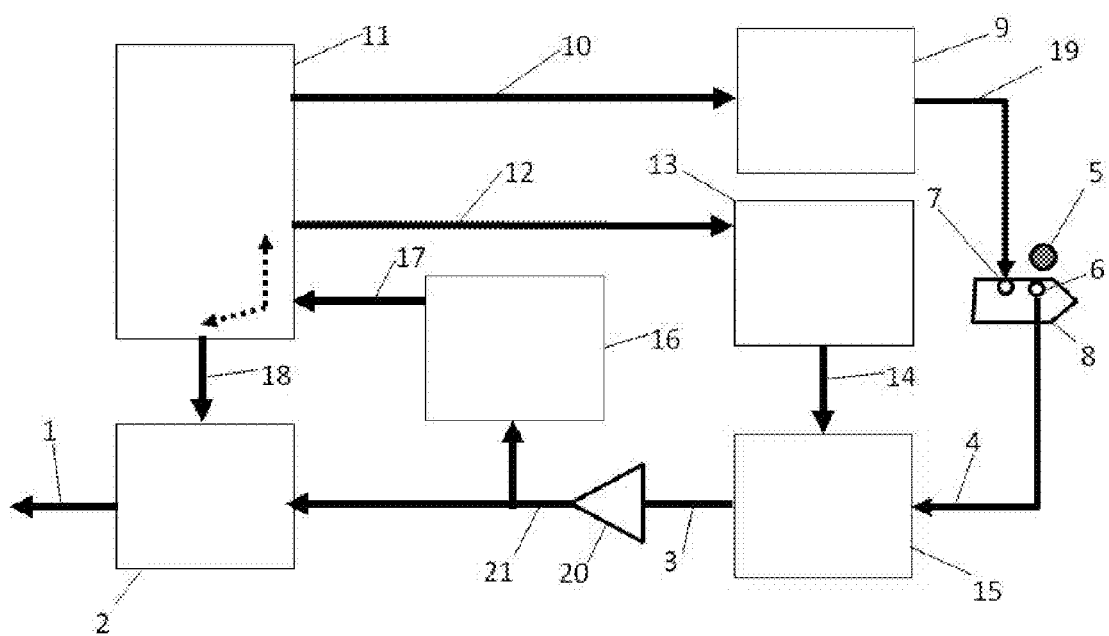
FIG. 7 is representing a bloc diagram with data flow of a method of the present embodiment.
Figure 8:
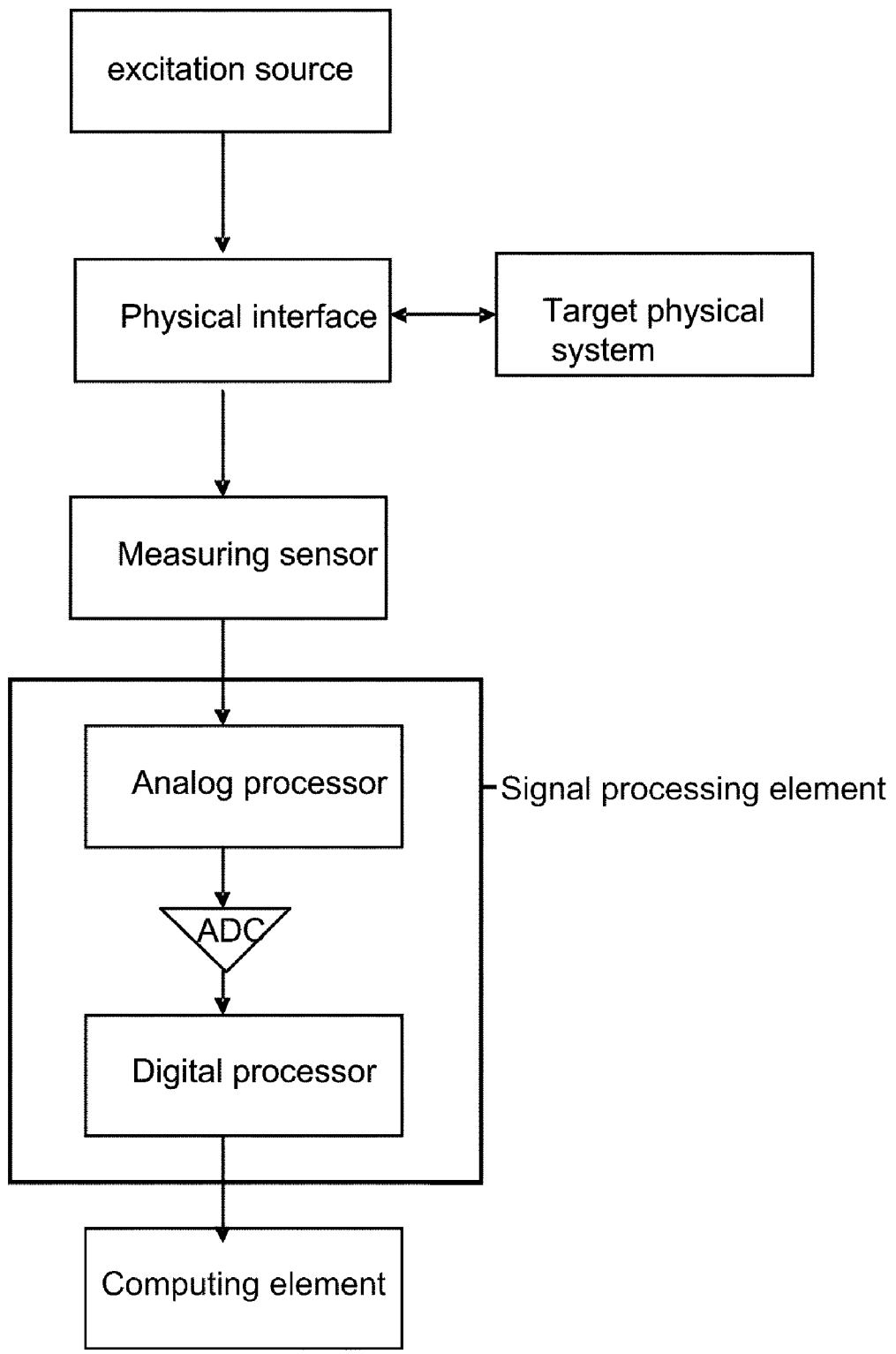
FIGS. 8, 9 and 10 are representing block schemas showing several embodiments according to the present embodiment.
Figure 9:
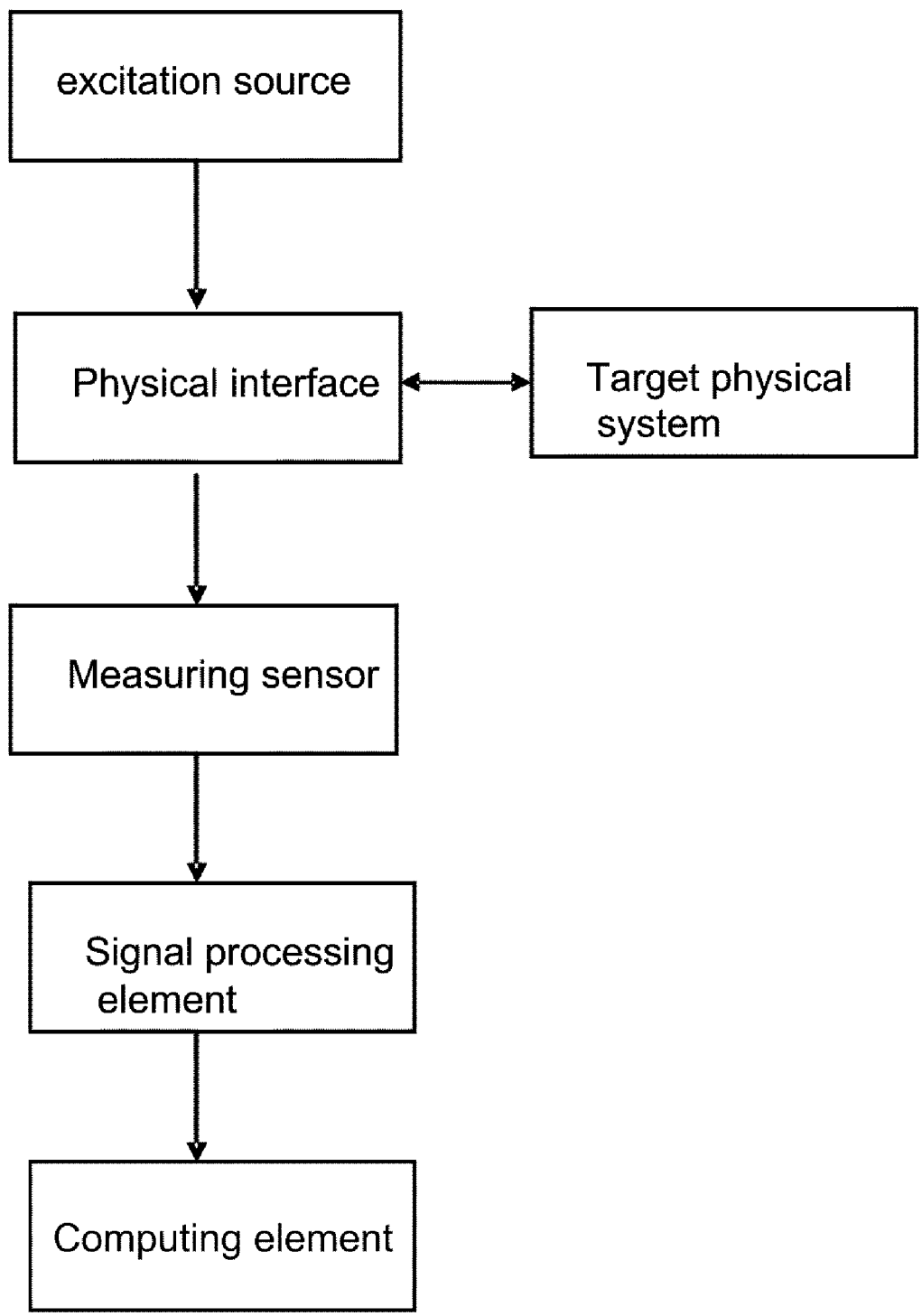
Figure 10:
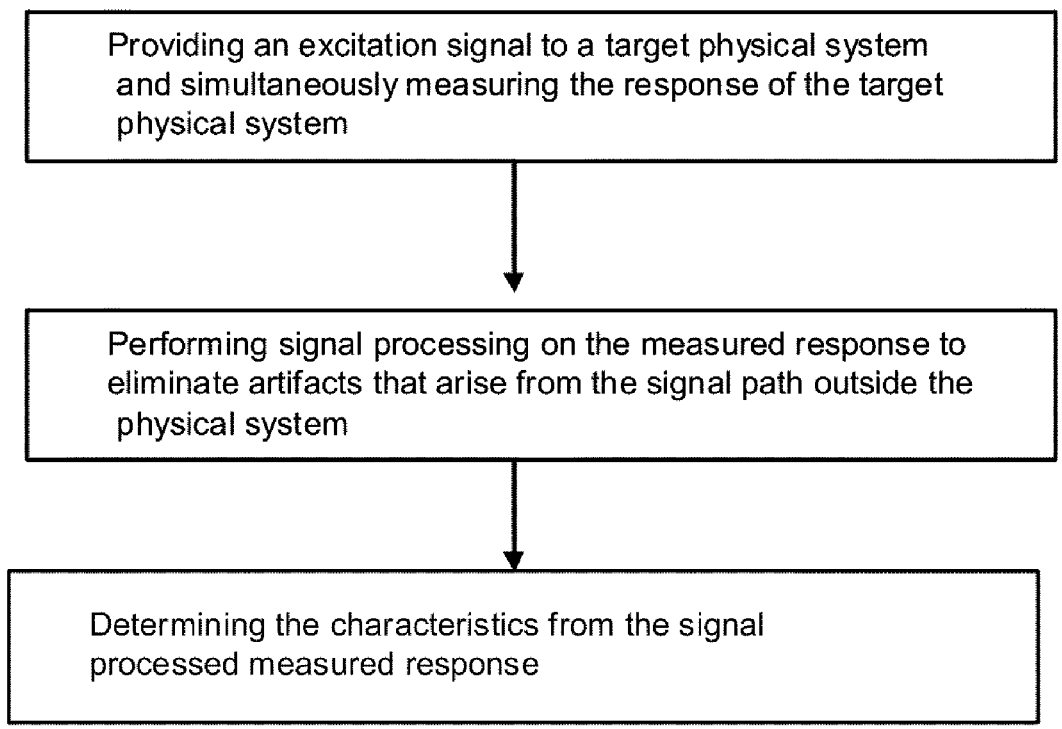

The general dataflow of the present embodiment is represented in FIG. 7, showing several preferred optional features. In that figure, the system is controlled by a digital process control unit 11. This digital process control unit 11 sends digital stimulus signal 10 to an analog stimulus generator 9. Said analog stimulus generator 9 sends analog stimulus signal 19 to a stimulating electrode 7 located on µm-sized probe 8 located close to the physical entity 5 to be characterized. Synchronously with the sending of the digital stimulus signal 10, the digital process control unit sends a digital template signal 12 to an analog template signal generator 13, which generate an analog template signal 14 to an analog read-out unit 15 comprising an analog compensator. Said compensator subtract the analog template signal 14 to the raw input signal 4 (measured signal), thereby producing an analog corrected signal 3. Said compensator can comprise a differential amplifier in the analog domain for subtracting the analog template signal 14 to the measured signal 4.

The analog corrected signal 3 is then sent to a digital to analog converter 20, which converts the analog corrected signal 3 into an analog corrected digital signal 21.

The analog corrected digital signal is sent to both a digital estimator 16, which estimate the intensity and duration of the residual artifact and a digital compensator 2. The output of the digital estimator 16 is sent to the process control unit 11 which decides whether the analog compensation is sufficient or if the digital template signal 12 has to be reestimated.

If the analog compensation is sufficient (i.e. the residual artifact is low and located in limited time regions), the process control unit sent a digital compensation signal estimate 18 to the digital compensator 2. The digital compensator then digitally corrects the analog corrected digital signal 21.

If the residual artifact, as is calculated by the digital estimator, is higher than a predetermined value, the process control unit switch the system into a training phase for reestimating the digital template signal 10. In such phase, a stimulus signal 19 is sent to the stimulating electrode 7, and the signal features originating from the physical entity 5 are filtered out of the measured signal 4 for example by means of a low-pass filter. The filtered signal is then used as a new template in subsequent measurement cycles.

Architecture

Figure 3:
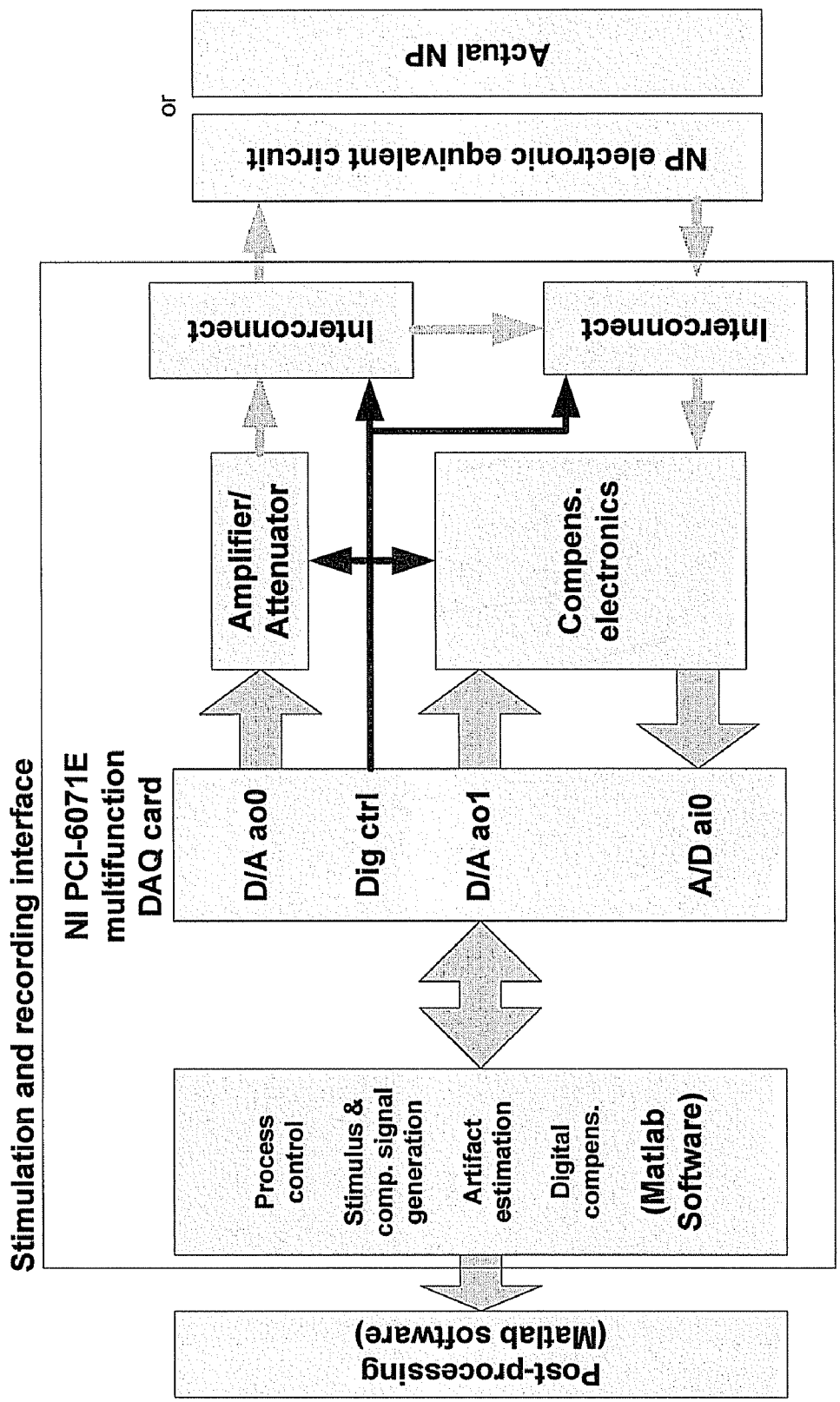
FIG. 3 is representing the architecture of a prototype unit able to perform the compensation of a stimulation artifact according to the method of the present embodiment.

An exemplary architecture uses a MATLAB-controlled NI DAQ card with external discrete electronics and two 12-bit D/A output (stimulus and compensation signal) and one 12-bit A/D input channel (recording). A common sampling rate of 500 kHz was used. This architecture is represented in FIG. 3.

Through a digitally-controlled interconnect and electronics, all pathways can be individually calibrated for gain, delay, and DC offsets. The system of the present embodiment operates in three steps which can be periodically repeated on demand:

(1) calibration of the electronics path,
(2) artifact estimation (training phase),
(3) artifact compensation during stimulation & recording.

During the training phase, a template of the artifact is constructed based on a comparison between stimulus and recorded data. This template is synchronously created during the compensation phase along with stimulation pulses and subtracted using a differential amplifier in the analog domain.

Remaining artifacts due to imperfect template subtraction are detected and compensated in the digital field.

SIMULATION/EXAMPLE

Figure 4:
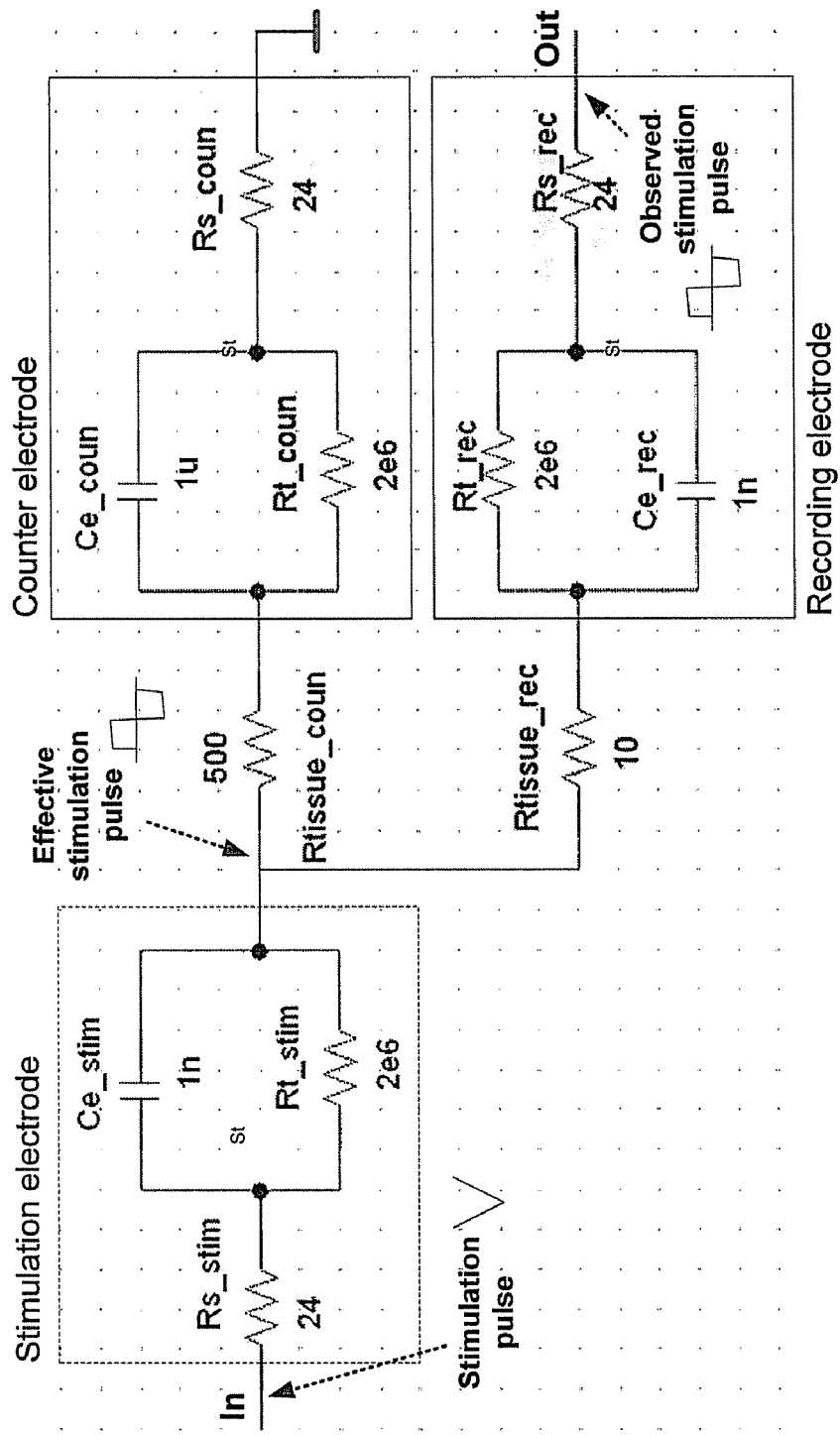
FIG. 4 is representing the linear equivalent circuit model of a neural probe configuration.

The exemplary system has been designed for arbitrary stimulus waveforms. Practical stimulus signals for neural stimulation are biphasic current pulses of 200 µs. Current pulses are used to maintain the waveform to the capacitive nature of the electrode-tissue contact. SPICE (Simulation Program with Integrated Circuit Emphasis) simulation results based on a measured and fitted neural probe equivalent model indicate that triangular voltage steering can be used as an alternative. The equivalent model is represented in FIG. 4. The non-linear voltage division between the stimulation and counter-electrode translates the triangular voltage signal into a double-trapezoid quasi-biphasic signal in the tissue. The recording electrode correctly records this signal.

For the closed-loop compensation, there is an alignment between the triangular stimulus waveform and the double-trapezoid recorded artifact signal. See FIG. 5.

Measurement Results

For closed-loop evaluation of the artifact compensation quality, the electronic equivalent circuit was built with discrete passive components and used as a device-under-test with the prototype system.

Figure 5:
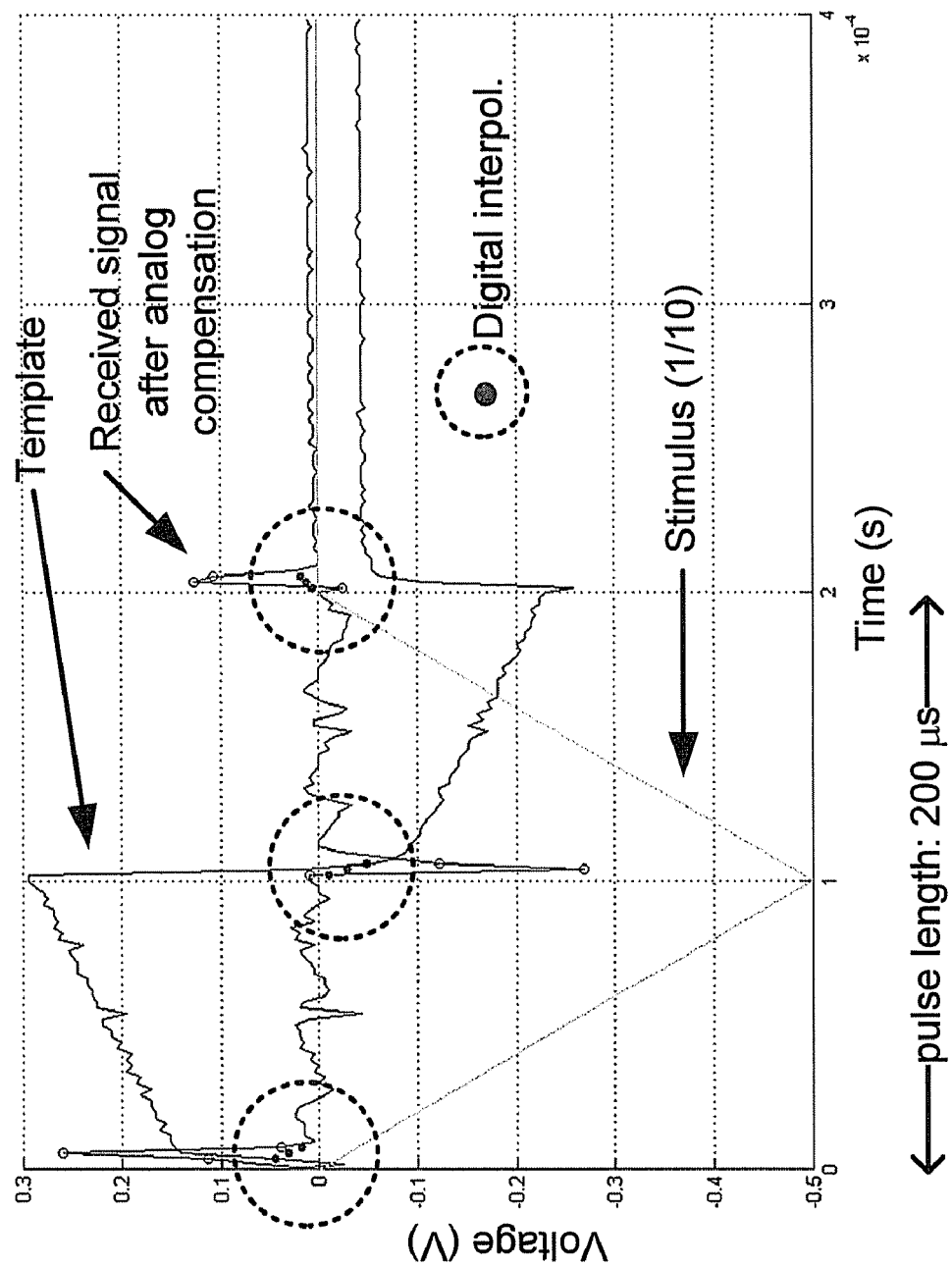
FIG. 5 is representing in the same drawing several time aligned measured signals wherein:
 (a) is the stimulation signal (scaled down by a factor 10),
 (b) is the template signal based on calibration,
 (c) is the received signal after analog compensation, and
 (d) is the received signal after blanking and digital interpolation (represented by dots).

The system was operated with triangular pulses (−5V peak, 200 µs) and a differential amplifier voltage gain of 10. All input and output signals were recorded (FIG. 5). The stimulus signal is recorded as a large double-trapezoid artifact signal (see curve b) and used as template. Analog compensation removes this component except for three narrow transition regions (see curve c). 3-point interpolation (see dots (d)) is used to remove these remaining artifact peaks.

Figure 6:
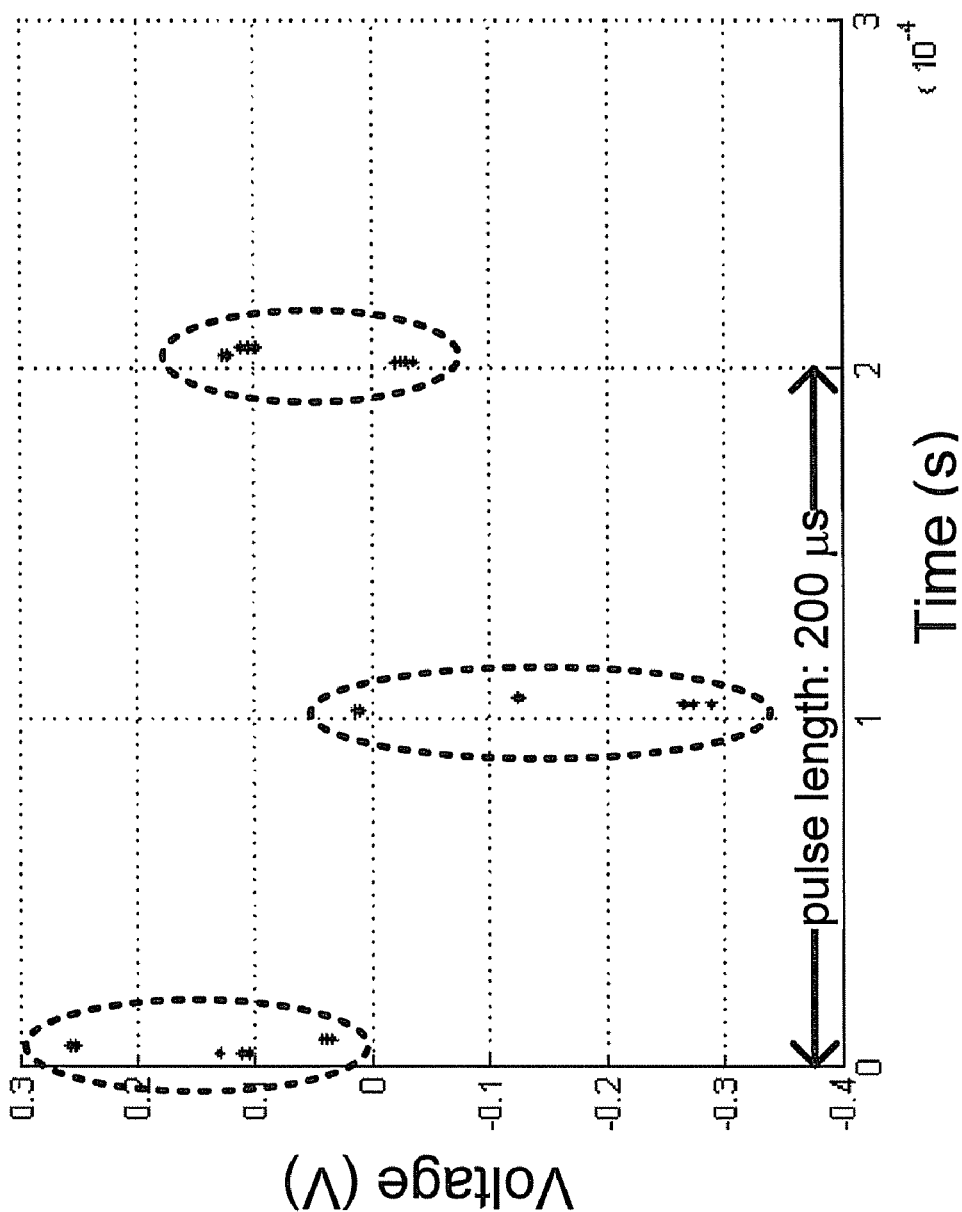
FIG. 6 is representing the distribution of the measured remaining artifact peak locations at the three edges of the trapezoid waveform represented in FIG. 5.

Peak distribution in 40 one-pulse measurements reveal that peaks essentially occur at 6 µs, 104 µs and 204 µs (FIG. 6), indicating a very low variance which can be exploited for reducing the remaining small-scale artifacts through interpolation. Measurements with pulse chains up to 10 ms and initial delays confirmed the low variance of the peak locations.

In order to quantitatively express the artifact reduction, the signal power was calculated by integrating the remaining artifact power within the pulse window for the different signals and normalization (Table 1).

TABLE 1

Normalized signal power within pulse window

|  | Norm. signal power |
|---|---|
| (1) Uncompensated artifact | 3656.93 |
| (2) After template subtraction | 2.20 |
| (3) After interpolation | 0.36 |

In the example, template subtraction reduces the average artifact voltage by a factor of about 40.8. The remaining artifact peaks were localized in 3×3 samples of a total duration of 18 µs which is less than 10% of the stimulation pulse duration.

Any external signal activity during calibration is removed through low-pass filtering. Blanking and/or 3-point digital interpolation reduces the average artifact voltage by an additional factor of 2.46. The combination of both methods leads to a reduction of the average stimulus artifact voltage by a factor of 40.8×2.46=100.5 being sufficient to avoid both saturation of the analog electronics and A/D converter and allow sufficiently high amplification to observe neural signals in the order of 50 $\mu V_{p-p}$ amplitude.

According to the present embodiment, the method reduces both the artifact in amplitude and time while being independent of the actual stimulus waveform.

Usual blanking techniques protect the analog electronics during stimulation but can make the recording side blind for several 100 µs. Adaptive filtering or spectral cancellation have a high signal processing complexity.

The present method allows template subtraction in a digitally-controlled analog hybrid context. Analog subtraction preserves dynamic range and linearity while the digital control allows tightly controlling timing and concentrating the remaining artifacts in well-known time regions. This present embodiment allows the present method and apparatus to operate both as an in situ monitoring system similar to as well as a closed-loop deep brain stimulation and recording system (DBSR) for an in vitro context.

The present method and apparatus are capable of handling arbitrary stimulus waveforms. They calibrate their own stimulation and recording signal paths using known signals in a feedback configuration.

Compensation is based on a hybrid approach using analog template subtraction based on a short training phase and digital interpolation.

In an exemplary embodiment, template subtraction reduces the average artifact voltage by a factor of 40, blanking and digital interpolation adds a further reduction of 2.5. Remaining artifact energy is spread over 10% of the stimulus pulse duration. This is an essential improvement over classical analog blanking. These methods and apparatus are easily extended to multiple channels. Higher gains for the recording amplifier can now be considered which will further improve the artifact reduction.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The invention claimed is:

1. A method for obtaining characteristics of a target physical entity comprising the steps of:
providing an excitation signal to the target physical entity and simultaneously measuring the response of the target physical entity;

performing analog signal processing on the measured response to eliminate artifacts that arise from a signal path outside the target physical entity;

determining the characteristics from the signal processed measured response, whereby the excitation signal and the analog signal processing are selected such that after analog signal processing of the measured signal, the analog measured signal contains artifacts which are localized in time.

2. The method of claim 1 wherein the analog signal processing step comprises the subtraction of a predetermined signal representative or corresponding to the signal path outside the physical entity to the measured signal.

3. The method of claim 1 wherein the analog signal processing step comprises the subtraction of a predetermined signal representative or corresponding to the signal path outside the physical entity to the measured signal, the predetermined signal being estimated by an initial training phase.

4. The method of claim 3 wherein the predetermined signal is estimated by low-pass filtering a measured response in a training phase.

5. The method of any of claim 3 comprising the step of estimating a residual artifact in the processed analog signal.

6. The method of claim 5 wherein an additional training phase is performed each time the residual artifact is above a predetermined threshold, defining a new predetermined signal to be used in subsequent stimulation sequences.

7. The method of claim 1 wherein the analog signal processing is followed by a digital signal compensation.

8. The method according to claim 7 wherein the digital compensation is obtained by interpolation, in particular three points interpolation, and/or blanking techniques and/or adapting filtering methods.

9. The method of claim 1 wherein the excitation of the target physical entity and the measurement of the response are done via electrodes.

10. The method of claim 1 wherein the excitation signal can be a voltage pulse, a current pulse or an RF pulse.

11. The method of claim 1, wherein the characteristics to be obtained are the electrical response of individual electrogenic cells to electrical stimuli corresponding to the excitation signal.

12. The method of claim 1 wherein the target physical entity is a single or a group of electrogenic cells.

13. The method of claim 1 wherein the target physical entity (system) is in vivo or in vitro single or limited group of neurons.

14. The method of claim 1 wherein the target physical system is bacteria, algae, fungi, protists or plants.

15. A system for obtaining characteristics of a target physical entity, the system comprising:

an excitation source for providing an excitation signal to the target physical entity and a sensor for simultaneously measuring the response of the target physical entity;

a signal processing element for performing signal processing on the measured response to eliminate artifacts that arise from a signal path outside the target physical entity; and a computing element for determining the characteristics from the signal processed measured response, wherein the system allows the selection of a predetermined excitation pulse and the signal processing element is selected such that after analog signal processing of the measured signal, the analog measured signal contains artifacts which are localized in time.

16. The system of claim 15 wherein the excitation source and sensor are located on a μm-sized probe able to discriminate individual action potential originating from a limited number of electrogenic cells.

* * * * *